United States Patent [19]

Boucher

[11] 4,119,439

[45] Oct. 10, 1978

[54] NAIL CLEANER

[76] Inventor: John L. Boucher, 4005 McLane Dr., Tampa, Fla. 33610

[21] Appl. No.: 789,196

[22] Filed: Apr. 20, 1977

[51] Int. Cl.² .............................................. B08B 3/02
[52] U.S. Cl. ................................... 134/183; 134/200; 128/366
[58] Field of Search .................... 4/165; 128/366, 368; 134/111, 198, 200, 199, 182, 183

[56] References Cited

U.S. PATENT DOCUMENTS

| | | | |
|---|---|---|---|
| 2,616,095 | 11/1952 | Stuckey | 134/111 X |
| 2,641,771 | 6/1953 | Schiro | 134/200 X |
| 3,220,424 | 11/1965 | Nelson | 128/368 X |
| 3,757,806 | 9/1973 | Bhaskar et al. | 134/199 X |
| 3,918,987 | 11/1975 | Kopfer | 134/199 X |
| 3,982,965 | 9/1976 | Spotz | 134/200 X |

*Primary Examiner*—Robert L. Bleutge
*Attorney, Agent, or Firm*—Arthur W. Fisher, III

[57] ABSTRACT

A nail cleaner for use in such areas as hospitals where sanitary conditions require cleaning beneath a person's fingernails, beauty salons, food, drug, electronic industries where hand cleaniness is required. The cleaner may also be used for industrial and commercial bathrooms and households/living quarters for normal cleaning and sanitary use, especially for young children where nail file tips are painful and may be detrimental to fingernails. The nail cleaner comprises a hood having an aperture formed therein for the placement of a person's hands therein and a basin cooperatively forming an enclosure for a nail cleaning operation. The nail cleaner further comprises a filter, a pump, a relief valve, and a spray manifold having a plurality of orifices formed therein to deliver a stream of water, detergent and antispetic solution through the orifices at a predetermined pressure wherein the person's fingers are held so that the streams of solution from the orifices engage the crevices between the person's fingers and his nails to dislodge and dissolve dirt.

3 Claims, 2 Drawing Figures

NAIL CLEANER

BACKGROUND OF THE INVENTION

1. Filed of the Invention

A nail cleaner for cleaning beneath a person's fingernails.

2. Description of the Prior Art

For a long time there has been available scrubbing machines which operate in a rotary fashion to rub a material such as a soaked cloth or bristles against the fingernail area and thus clean dirt from therebeneath.

The prior art also includes sanitary scrub sinks for the cleaning of one's hands a sanitary fashion.

The machines currently in use for cleaning nails are complex and not very sanitary. What is needed is a sanitary nail cleaner which is simple to build and operate for such in such areas as hospitals, beauty salons, food, drug, electronic industries where hand cleanliness is required. The cleaner may also be used for industrial and commercial bathrooms and households/living quarters for normal cleaning and sanitary use, especially for young children where nail file tips are painful and may be determental to fingernails.

In addition nail file tips are used to scrape dirt from under the nail. The use of this device is sometimes painful, especially for children, and also detrimental because of the resulting recession of the nail adhering extremity to the finertip.

Examples of the prior art are shown in U.S. Pat. Nos. 2,424,509; 3,216,034; 3,358,747; and 3,728,745.

SUMMARY OF THE INVENTION

The present invention relates to a nail cleaner for use in such areas as hospitals where sanitary conditions are required for cleaning beneath a person's fingernails, beauty salons, food, drug, electronic industries where hand cleanliness is required. The cleaner may also be used for industrial and commercial bathrooms and households/living quarters for normal cleaning and sanitary use, especially for young children where nail file tips are painful and may be detrimental to fingernails.

The nail cleaner comprises a basin and a hood attached thereto so as to cooperatively form an enclosure for a nail cleaning operation. The nail cleaner comprises a water, detergent and antiseptic solution delivery means to provide a high pressure discharge of solution within the enclosure. The delivery means includes a filter, a pump, a relief valve, and a spray manifold having a plurality of orifices formed therein. The pump is operated to discharge the solution at a predetermined discharge pressure so that the solution is discharged from the orifices at a predetermined orifice discharge pressure.

The hood includes an aperture formed therein of sufficient size for a person to place his hands therethrough. The hood may be constructed of a transparent material for the observation of the nail cleaning operation.

The diameter of each orifice is preferably between 2mm. and 0.1mm. The predetermined orifice discharge pressure is between 75 psi and 200 psi depending on the desired cleaning speed, orifice size and manifold thickness.

During operation the pump is turned on and a person inserts a hand through the aperture and disposes his fingertips in close promixity to the plurality of orifices such that the streams of solution engage the crevices between the person's fingers and the nails to dislodge and dissolve dirt.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
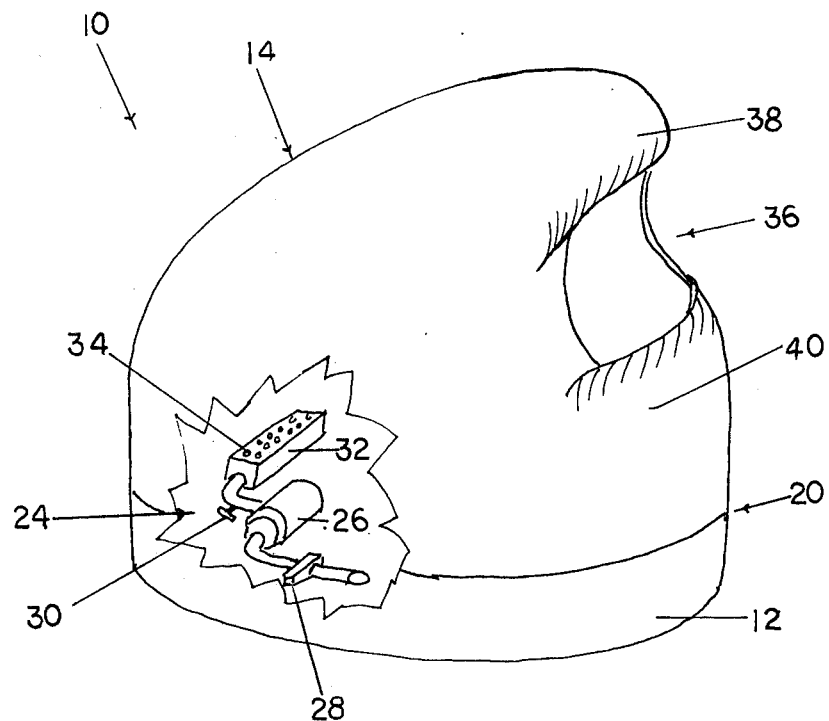
FIG. 1 is a perspective view of the nail cleaner with a section of the enclosure cut away to show the cleaning solution delivery means.

As shown in FIG. 1, the present invention relates to a nail cleaner generally indicated as 10 for cleaning beneath a person's fingernails for use in such areas as hospitals where sanitary conditions are required.

The nail cleaner 10 comprises a substantially cylindrical basin 12 forming the base thereof and a hood 14 detachably attached to the basin 12 along the perimeter thereof by means of an inner lip 16 on the hood 14 which engages an outer lip 18 on the basin 12 so that the basin 12 and hood 14 cooperatively form an enclosure 20 for nail cleaning operation hereinafter described. The basin 12 includes an outlet means 22 for the removal of solution therefrom when necessary. Of course, removal of solution would be performed by removing hood 14 and simply emptying and rinsing basin 12 as would be done for any simple wash basin. Nail cleaner 10 is recharged with solution simply by pouring the solution in the basin until level reaches a pre-determined indicated level.

The nail cleaner 10 further comprises a cleaning solution delivery means 24 to provide a high pressure discharge of cleaning solution (water, and/or antiseptic solution) within the enclosure 20. The delivery means 24 includes a pump 26, a filter 28 operatively coupled to the inlet to the pump 26, a sping-loaded relieve valve 30 operatively coupled to the outlet of the pump 26 and a spray manifold 32 having a plurality of orifices 34 formed therein. The spray manifold 32 is operatively coupled to the outlet of the relief valve 30 and removable for easy cleaning.

The pump 26 is of a positive displacement type such as a gear pump to provide a constant predetermined pump outlet pressure which directly corresponds to a predetermined delivery pressure. The relief valve 30 may be adjustable to provide different outlet pressures depending on the desired delivery pressure. The relief discharge from the relief valve 30 is into the basin 12. The inlet of the pump 26 is flooded from the basin 12 wherein cleaning solution is recovered and recycled. The solution is filtered in the filter 28 before entering the pump 26. It is then discharged from the pump 26 through the relief valve 30 at the predetermined outlet pressure, and then discharged through the orifices 34 at the predetermined delivery pressure.

The hood 14 includes an aperture 36 formed therein of sufficient size for a person to comfortably pass his hand therethrough. The hood 14 may be constructed of a transparent material such as clear plastic or glass so that the user can observe the nail cleaning so that he can more easily clean his nails. To minimize the splashing of any cleaning solution therethrough the aperture 36 should be no larger than the size required for a person to comfortably pass his hands therethrough.

Figure 2:
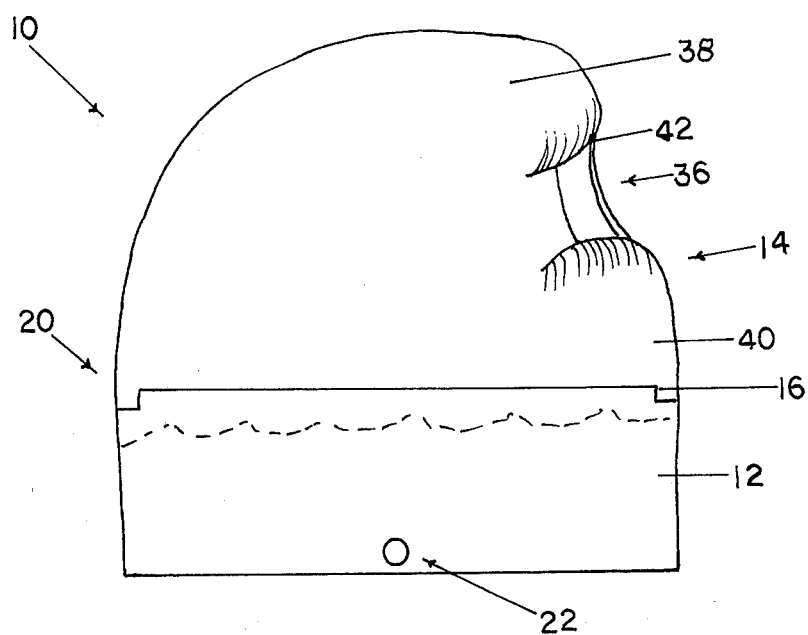
FIG. 2 is a partial side cross-section view of the upper portion of the nail cleaner.

As best shown in FIG. 2, the hood 14 has curved surfaces to minimize splashing comprising an upper portion 38 and a lower portion 40 wherein the aperture 36 is disposed substantially rearward (approximately a quarter of the distance from front to rear) of the front of the nail cleaner 10. The hood 14 includes a skirt 42 extending inwardly from the inner periphery of the aperture 36. The diameter of each orifice 34 is between 2.0mm and 0.1mm although for optimum performance, a diameter of 0.5mm to 0.7mm has been found to be the most efficient size for nail cleaning.

The predetermined delivery pressure is between 75 psi and 200 psi.

The distance between the aperture 36 and the orifice 34 is substantially equal to the distance between an average person's wrist and the tips of his fingers so that during the nail cleaning operation, only the person's hand fits inside the nail cleaner 10 and therefore only his hands are exposed to the cleaning solution.

The basin 12 and the hood 14 are detachable interconnected by a connecting means generally indicated as 44 to prevent leakage during operation and permit detachment for cleaning. Specifically the connecting means 44 comprises an inner lip 16 formed on the basin 12 and an outer lip 18 formed over the hood 14 overlaying the basin lip 16.

During operation, the pump 26 is turned on and the person alternately inserts his hands through the aperture 36 and disposes his fingertips in close proximity to the plurality of orifices 34 and discharge of cleaning solution such that the streams of cleaning solution discharged from the orifices 34 at the predetermined delivery pressure engage the crevices between the persons fingertips and his nails to dislodge and dissolve dirt. The tips of the thumb and fingers can be pressed together while applying a slight shear movement to further expose the crevices for even more efficient cleaning. During the same operation, the person may also wash his hands.

The used cleaning solution falls into the basin 12 where it is recycled through the delivery means 24 passing through the filter 28 for the removal of impurities. Periodically, the solution should be drained and new solution added through a make-up means (not shown).

It will thus be seen that the objects set forth above, among those made apparent from the preceding description are efficiently attained and since certain changes may be made in the above construction without departing from the scope of the invention it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A nail cleaner for cleaning beneath a person's fingernails comprising an enclosure having a basin forming the base thereof and an enlarged hood detachably attached to said basin along the perimeter thereof, an aperture formed in said enlarged hood for placing the person's hand therethrough, said aperture being disposed rearward of the front of said enlarged hood and including a skirt extending inwardly from the inner periphery thereof to prevent splashing, and a cleaning solution delivery means comprising a pump having supply source of cleaning solution and a spray manifold disposed within said enclosure operatively coupled to the outlet of said pump, said spray manifold including a plurality of orifices to discharge a cleaning solution at a predetermined delivery pressure disposed laterally relative to said aperture and perpendicular to said aperture so as to permit cleaning beneath the person's fingernails within said enclosure whereby cleaning solution engages the crevices between the person's fingertips and fingernails to dislodge and dissolve dirt.

2. The nail cleaner of claim 1 wherein said predetermined delivery pressure is between 75 psi and 200 psi.

3. The nail cleaner of claim 1 wherein the diameter of each of said orifice is between 2.0mm and 0.1mm.

* * * * *